US012616852B2

(12) United States Patent
Helander et al.

(10) Patent No.: US 12,616,852 B2
(45) Date of Patent: May 5, 2026

(54) METHODS AND SYSTEM RELATED TO RADIOTHERAPY TREATMENT PLANNING

(71) Applicant: RaySearch Laboratories AB (Publ), Stockholm (SE)

(72) Inventors: Rasmus Helander, Johanneshov (SE); Mats Holmstrom, Varmdo (SE)

(73) Assignee: Raysearch Laboratories AB, Stockholm (SE)

( * ) Notice: Subject to any disclaimer, the term of this patent is extended or adjusted under 35 U.S.C. 154(b) by 0 days.

(21) Appl. No.: 18/851,085

(22) PCT Filed: Feb. 7, 2023

(86) PCT No.: PCT/EP2023/052907
§ 371 (c)(1),
(2) Date: Sep. 26, 2024

(87) PCT Pub. No.: WO2023/193977
PCT Pub. Date: Oct. 12, 2023

(65) Prior Publication Data
US 2025/0108233 A1 Apr. 3, 2025

(30) Foreign Application Priority Data
Apr. 5, 2022 (EP) ..................................... 22166799

(51) Int. Cl.
*A61N 5/10* (2006.01)

(52) U.S. Cl.
CPC ......... *A61N 5/1031* (2013.01); *A61N 5/1045* (2013.01)

(58) Field of Classification Search
CPC .. A61N 5/1031; A61N 5/1038; A61N 5/1039; A61N 5/1045; A61N 2005/1041
See application file for complete search history.

(56) References Cited

U.S. PATENT DOCUMENTS

| | | | | |
|---|---|---|---|---|
| 11,011,264 B2* | 5/2021 | Zankowski | ............ | G16H 50/20 |
| 11,020,615 B2* | 6/2021 | Eriksson | .............. | A61N 5/1031 |
| 11,167,152 B2* | 11/2021 | Liu | ........................ | A61N 5/103 |

(Continued)

FOREIGN PATENT DOCUMENTS

| | | |
|---|---|---|
| CN | 109843377 A | 6/2019 |
| CN | 110944717 A | 3/2020 |

(Continued)

OTHER PUBLICATIONS

International Search Report and Written Opinion dated Apr. 24, 2024, European Patent Office, Rijswijk, Netherlands.

(Continued)

*Primary Examiner* — Sean M Luck
(74) *Attorney, Agent, or Firm* — Noréns Patentbyrå Ab

(57) ABSTRACT

The present disclosure relates to the use of machine learning for determining initial machine setting parameters for radiotherapy treatment planning. A machine-learning system is trained on data sets including a dose distribution and a set of machine parameter settings resulting from that dose distribution. The trained system can be used for determining machine parameter settings based on a desired dose distribution, which may be used as initial machine parameter settings for radiation treatment optimization.

12 Claims, 2 Drawing Sheets

(56) References Cited

U.S. PATENT DOCUMENTS

| | | | | |
|---|---|---|---|---|
| 2005/0143965 A1* | 6/2005 | Failla | ...................... | G01T 1/02 |
| | | | | 703/2 |
| 2011/0153547 A1* | 6/2011 | McNutt | ................... | G06N 5/02 |
| | | | | 706/54 |
| 2014/0350863 A1* | 11/2014 | Hartman | .............. | A61N 5/1031 |
| | | | | 702/19 |
| 2015/0095043 A1* | 4/2015 | Cordero Marcos | .... | G16H 20/40 |
| | | | | 705/2 |
| 2016/0129282 A1* | 5/2016 | Yin | ........................ | G16H 40/20 |
| | | | | 600/1 |
| 2016/0140300 A1* | 5/2016 | Purdie | ................... | G16H 20/40 |
| | | | | 705/2 |
| 2017/0177812 A1* | 6/2017 | Sjölund | .................. | G16H 20/40 |
| 2017/0304651 A1* | 10/2017 | Takayanagi | .......... | A61N 5/1043 |
| 2018/0063386 A1* | 3/2018 | Sharma | .................. | H04N 23/60 |
| 2018/0304097 A1* | 10/2018 | Bokrantz | .......... | G06F 16/90335 |
| 2019/0030370 A1* | 1/2019 | Hibbard | .............. | A61N 5/1067 |
| 2019/0192880 A1* | 6/2019 | Hibbard | ................ | G16H 30/20 |
| 2019/0333623 A1* | 10/2019 | Hibbard | .............. | A61N 5/1039 |
| 2020/0043573 A1* | 2/2020 | Fält | ........................ | G16H 40/63 |
| 2020/0188692 A1 | 6/2020 | Liu | | |
| 2020/0360728 A1* | 11/2020 | Tilly | ................... | A61N 5/1081 |
| 2021/0035340 A1* | 2/2021 | Wang | ..................... | G06V 10/82 |
| 2021/0339046 A1* | 11/2021 | Lachaine | ............. | A61N 5/1037 |
| 2022/0054859 A1* | 2/2022 | Liu | ........................ | G06N 20/00 |
| 2022/0088410 A1* | 3/2022 | Hibbard | .............. | A61N 5/1038 |

FOREIGN PATENT DOCUMENTS

| | | |
|---|---|---|
| CN | 113891742 A | 1/2022 |
| KR | 1020200116766 A | 10/2020 |
| WO | 2019023142 A1 | 1/2019 |
| WO | 2020256750 A1 | 12/2020 |

OTHER PUBLICATIONS

Extended European Search Report dated Sep. 19, 2022, European Patent Office, Munich, Germany.

Offie Action dated Feb. 22, 2025 in corresponding Chinese application No. CN110944717A, Chinese Patent Office, Beijing, China.

Fan et al. "Verification of the machine delivery parameters of a treatment plan via deep learning". Phys Med Biol. 65 (19): 195007. doi:10.1088/1361-6560/aba165.

Office Action dated Apr. 9, 2025 in corresponding Japanese application No. 2024-552403, Japanese Patent Office, Tokyo, Japan.

* cited by examiner

METHODS AND SYSTEM RELATED TO RADIOTHERAPY TREATMENT PLANNING

TECHNICAL FIELD

The present invention relates to radiotherapy treatment plan optimization and in particular to parameter initialization for such optimization procedures.

BACKGROUND

In radiotherapy treatment plan optimization, an optimization problem is set up and the radiotherapy treatment plan is optimized to achieve a desired dose distribution in the patient, given a set of variables which typically include machine parameters of the radiotherapy treatment apparatus that is to be used. The initial values for these parameters may be set in different ways.

For photon treatment, machine parameters typically include MLC leaf sequencing. These initial machine parameter values may be determined by solving a fluence map optimization problem and subsequently performing a conversion from the optimized fluence map dose to feasible machine parameters. This involves target projection, fluence map optimization, and conversion to machine parameters. This is a time-consuming process and the conversion step is generally a source of inaccuracy in the planning procedure, which leads to long optimization times since many iterations are needed.

For ion therapy, such as proton therapy, machine parameters include spot placement, spot weights and beam energy. For pencil beam scanning, as an example, the initial value of these parameters can be set in a number of different ways and implementation varies across different clinics. One possible implementation includes computing target projections and subsequently using some mathematical formula to decide initial values for the spot weights.

The present disclosure aims at making the treatment plan optimization procedure faster and enable better treatment plans resulting from the treatment plan optimization procedure.

SUMMARY OF THE INVENTION

The present disclosure relates to the use of machine learning for determining initial machine setting parameters for radiotherapy treatment planning. Accordingly, the disclosure relates to a computer-based method of training a machine learning system including inputting to the machine learning system a plurality of data sets, each data set including one or more dose distributions and a set of machine parameter settings including at least one machine parameter setting resulting from the one or more dose distributions in a planning procedure, to train the machine learning system to output a set of at least one machine parameter setting based on a reference dose distribution.

The disclosure also relates to a machine learning system which has been trained according to the above. Said machine learning system is arranged to take input data in the form of one or more dose distribution and output at least one machine parameter setting that will is suitable for producing the dose distribution for a particular radiotherapy delivery apparatus.

The disclosure also relates to a computer-based method using such a machine-learning system for determining machine parameter settings. The method includes the step of inputting one or more reference dose distributions into the machine learning system, performing parameter initialization by the machine learning system and outputting from the machine learning system a set of machine parameter settings including at least one machine parameter setting for a radiotherapy delivery apparatus. By basing the machine parameter settings on knowledge about suitable machine parameter settings for similar dose distributions, a better set of machine parameter settings can be obtained.

Hence, according to the invention, more correct input data regarding machine parameters of the radiation therapy delivery apparatus can be obtained in an efficient way by means of machine-learning. This means that the plan optimization times can be shortened since the initial data will be more correct. The method is particularly useful for machine parameter initialization for use in machine learning based optimization, but it is also useful for any other type of optimization procedure.

For photon treatment, the set of machine parameter settings may include one or more of MLC leaf settings, MU settings, start and stop angles, couch angles, and pitch. For Intensity Modulated Radiation Therapy (IMRT) applications, the set of machine parameter settings may include one or more of Segmental MLC (SMLC) or Dynamic MLC (DMLC). For ion treatment, such as proton treatment, the set of machine parameter settings may include, for example, one or more of spot placement, spot weights and beam energy.

The disclosure also relates to a computer-based radiotherapy treatment plan optimization method including, before performing the plan optimization, performing the method of determining a set of machine parameter settings according to any of the embodiments outlined above, and using the resulting set of machine parameter settings as an initial setting for the corresponding machine parameters in the radiotherapy treatment plan optimization.

The machine parameter setting, or settings, determined according to the above can be used for any optimization procedure where a reference dose can be generated in order to guide the prediction of initial machine parameters that are to be used as optimization variables. A few examples of such optimization procedures are:

Dose mimicking optimization as implemented in machine learning planning, where a machine learning model predicts the reference dose, which is then converted to a deliverable dose by dose mimicking optimization Multi-criteria optimization (MCO), where a reference dose is calculated from fluence maps and then optimized using dose mimicking by optimizing more than one objective function at the same time.

Where a plan has already been optimized for delivery by one delivery machine, recreating the same dose distribution for delivery by a different delivery machine, by using the original plan as a reference dose distribution for dose mimicking optimization.

Conventional inverse planning for Volumetric Modulated Arc Therapy (VMAT), where optimized fluence maps are used to calculate the reference dose (in this case, the invention replaces the leaf conversion algorithm).

The methods according to this disclosure may be used for any treatment modality, including both photon and ion-based modalities such as proton treatment, or carbon or helium ion treatment.

The disclosure also relates to a computer program product comprising computer readable code means which, when run in a computer will cause the computer to perform any of the methods outlined above. The computer program product may comprise non-transitory storage means having stored thereon the computer-readable code means. the disclosure also relates to a computer comprising a processor and a program memory, said program memory having stored thereon a computer program product.

BRIEF DESCRIPTION OF DRAWINGS

The invention will be described in more detail in the following, by way of examples and with reference to the appended drawings.

DETAILED DESCRIPTION OF EMBODIMENTS

Figure 1:
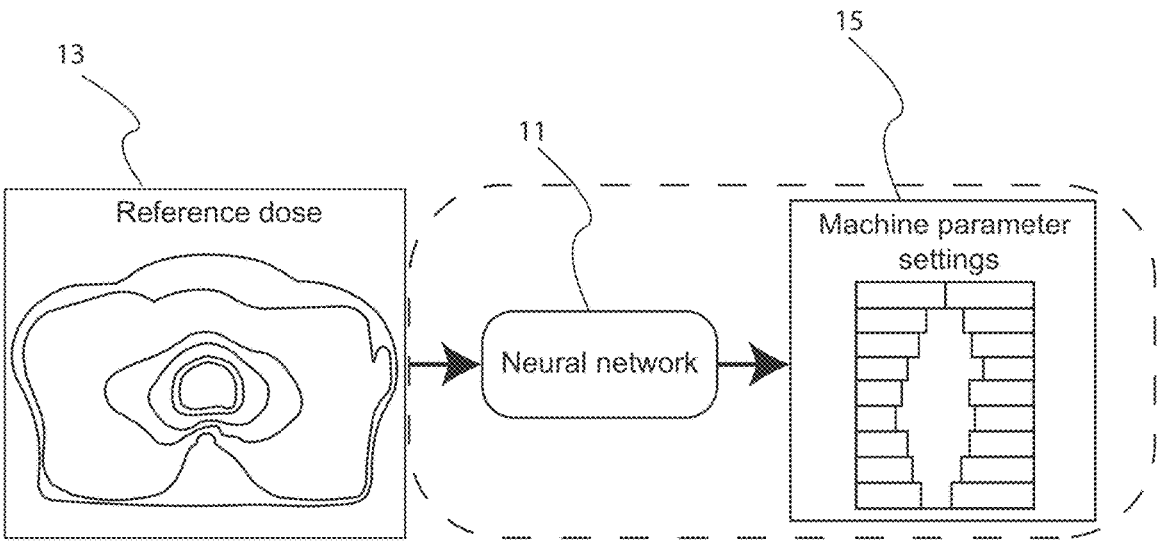
FIG. 1 illustrates generally the steps of obtaining machine parameter settings per the present disclosure.

The disclosure relates to a method of training a machine learning system to return suitable machine parameter settings for a radiotherapy treatment plan based on one or more reference doses. Such machine parameter settings reflect the capabilities of the radiation delivery apparatus to be used for delivering the plan. For photon-based plans the parameter settings may be related to MLC leaf positions and/or other parameters such as monitor units (MU), start and stop angles, couch angles and pitch, where pitch is the possible tilting of the patient support. For proton- or other ion-based plans, other parameter settings may be relevant, such as spot positions, spot weights and beam energy. The disclosure also relates to a method for using a machine learning system trained in this way to obtain machine parameter settings for a radiotherapy treatment plan. The machine learning system may be any type of machine learning system, including a neural network such as a deep neural network.

Exactly which machine parameter settings are needed depends on the delivery system to be used for delivering the plan. The machine learning system may be adapted to determine all applicable machine parameter settings, or just a subset of them. The ones that are not determined by the machine learning system must be provided by some other method.

The parameter settings returned from the trained neural network may be used as initial values to a treatment planning procedure. The treatment planning procedure may be any suitable planning method, such as dose mimicking, or a traditional optimization procedure using an optimization problem. Such procedures are known in the art and typically use an optimization problem designed to ensure a suitable dose distribution, corresponding to the reference dose distribution or distributions, over the treatment area, possibly along with other objectives such as treatment time. The machine parameter settings that have been determined based on the reference dose distribution or distributions are used as initial values for the optimization variables.

For application in a dose mimicking procedure, input data to the optimization process include one or more reference dose distributions, where each reference dose distribution is a 3D volume with dose values corresponding to the desired dose distribution for the patient. The dose distribution may be generated in any suitable way. For example, the reference dose may be an ML-predicted dose, a fluence map optimized dose, or a dose obtained from another plan or treatment technique that is to be mimicked.

Input data sets to the training process for training the machine learning system include sets of machine parameter settings and the dose distributions resulting from each set of machine parameter settings, which may, for example, be a clinical plan. The machine parameter settings therefore constitute the solution that is considered to be correct in view of the dose distribution of the same input data set.

FIG. 1 illustrates an example of the procedure of obtaining machine parameter settings by means of a machine learning system 11. As will be understood, the nature of the machine parameter settings returned from the process will differ depending on treatment modality and the type of delivery apparatus that will be used in the treatment. On the left-hand side is a reference dose distribution 13 that will be used as input data to the machine learning system 11. This is the dose distribution that the patient should ideally receive. The reference dose distribution in this example is given as slices of dose. The machine learning system is a Unet model. The function of such models is well known in the art.

Figure 2:
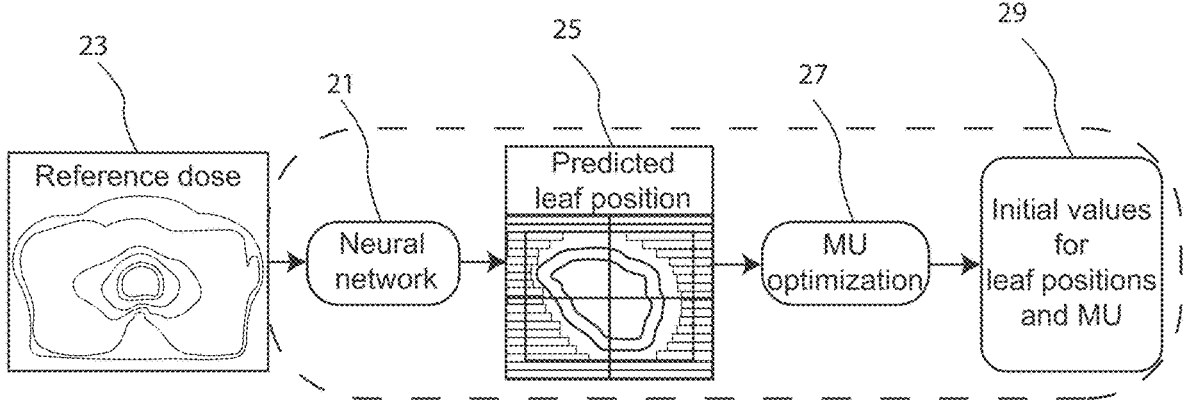
FIG. 2 illustrates the steps of obtaining machine parameter settings for photon-based treatment according to an embodiment.

FIG. 2 illustrates an example for photon-based treatment. As in FIG. 1, a machine learning system 21 receives input data in the form of a reference dose distribution 23, which is the desired dose distribution for use in the treatment of a patient, and returns machine parameter settings. In FIG. 2, a subset of the parameter settings is returned in the form of MLC leaf positions 25. The output from the machine learning system in this example is a leaf opening matrix shown schematically with reference numeral 15, defining the leaf positions of the MLC to be used in the treatment plan optimization.

In this example, MU settings are needed but are not determined by the machine learning system. Therefore, an MU optimization 27 is performed based on the machine parameter settings, returning initial values for MU. Alternatively, the initial MU setting may be predicted, or determined in any other suitable way and used in the subsequent optimization.

Figure 3:
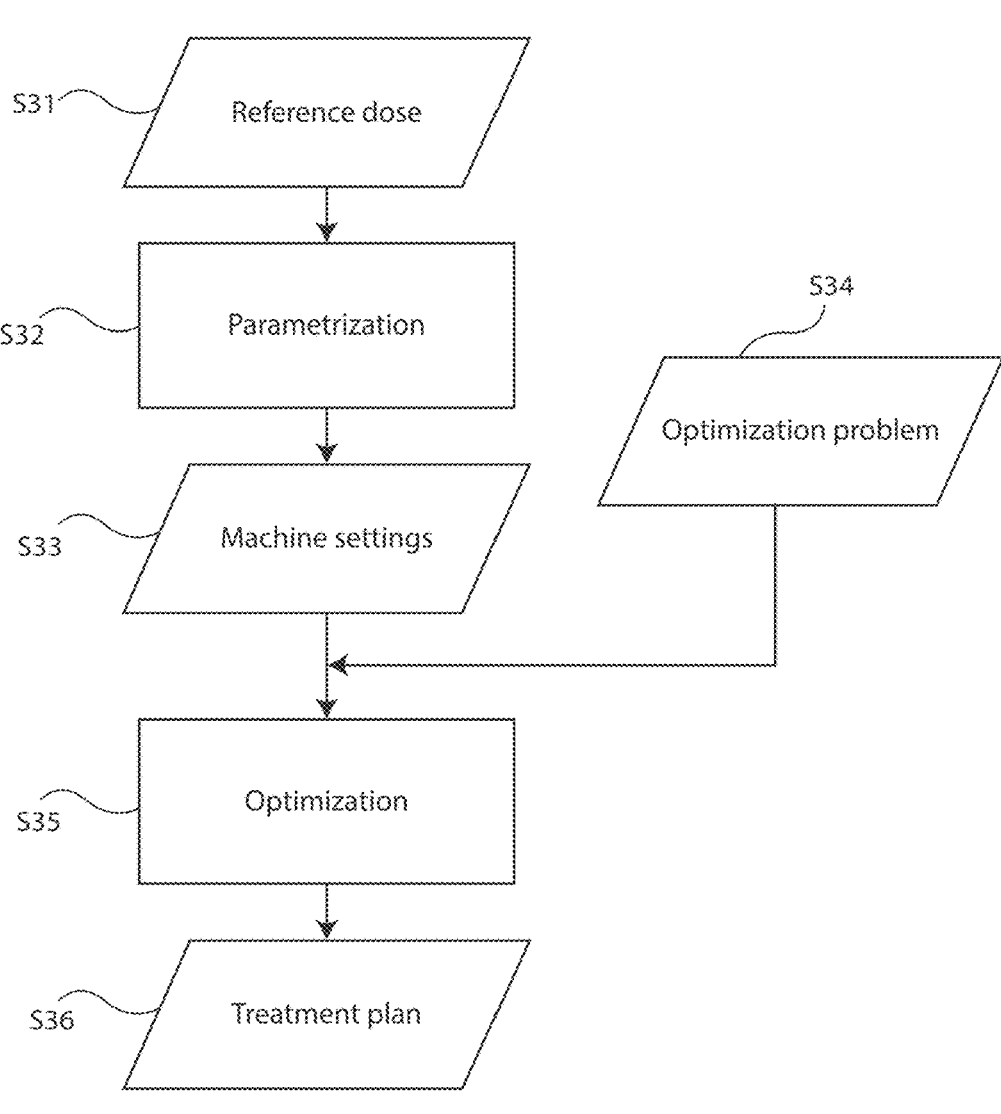
FIG. 3 is a flow chart of a treatment plan optimization method using the inventive method for parameter optimization.

FIG. 3 illustrates the overall flow of treatment plan optimization incorporating the steps according to embodiments of the invention. To begin with, steps corresponding to the disclosure of FIG. 1 are performed. A reference dose S31 corresponding to the desired dose distribution for a patient is input into a machine-learning system that has been trained as outlined above for parametrization S32. The output S33 from the parametrization procedure includes machine parameter settings for the delivery apparatus to be used in the treatment. These output machine parameter settings, and an optimization problem S34 are used as an input to an optimization procedure S35. The optimization problem S34 and the optimization procedure S35 may be as conventionally used in the art. The initial steps S31-S33 therefore replace the steps conventionally performed to provide the machine parameter settings, including target projection, fluence map optimization and leaf sequencing. As will be understood, utilizing a machine learning system that is able to provide these parameter settings S33 directly from the reference dose saves time and effort.

The optimization procedure in step S35 may rely on one of the following methods:

Dose mimicking optimization as implemented in machine learning planning, where a machine learning model predicts the reference dose, which is then converted to a deliverable dose by dose mimicking optimization Multi-criteria optimization (MCO), where a reference dose is calculated from fluence maps and then optimized using dose mimicking by optimizing more than one objective function at the same time.

Where a plan has already been optimized for delivery by one delivery machine, recreating the same dose distribution for delivery by a different delivery machine, by using the original plan as a reference dose distribution for dose mimicking optimization.

Conventional inverse planning for Volumetric Modulated Arc Therapy (VMAT), where optimized fluence maps are used to calculate the reference dose (in this case, the invention replaces the leaf conversion algorithm).

Figure 4:
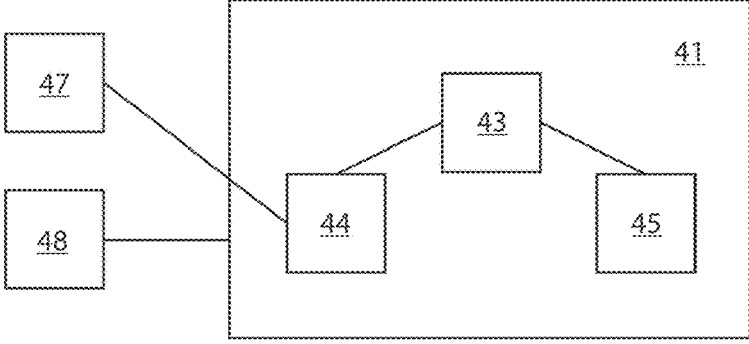
FIG. 4 is a schematic drawing of a computer arranged to perform one or more of the methods according to the present disclosure.

FIG. 4 is a schematic drawing of a computer arranged to perform one or more of the methods according to the disclosure. A computer 41 comprises a processor 43, a data memory 44 and a program memory 45. Preferably, one or more user input means 47, 48 is also present, in the form of a keyboard, a mouse, a joystick, voice recognition means and/or any other available user input means. The user input means may also be arranged to receive data from an external memory unit.

The program memory 45 holds a computer program arranged to control the processor to perform the procedure. Like the data memory 44, the program memory may also be implemented as one or several units as is seen fit. The data memory 44 holds input data that may be used in the respective procedure, and output data resulting from the planning. Input data to the training procedure includes training data sets. Input data to the method of determining machine parameter settings include one or more reference dose distributions. Input data to the method of optimizing a plan includes objective functions, derived, for example, from reference dose distribution(s) and clinical goals.

The invention claimed is:

1. A computer-based method, executed on a radiotherapy treatment planning system, comprising:

inputting to a machine learning system a plurality of historical data sets, each data set including a dose distributions and a corresponding set of machine parameter settings used to deliver the dose distributions;

training the machine learning system, based on the historical data sets, to generate machine parameter settings from a reference dose distribution, wherein the machine parameter settings correspond to initialization values used by a radiotherapy treatment plan optimization algorithm;

generating, using the trained machine learning system, an initial set of machine parameter settings from a reference dose distribution associated with a patient, the initial set being directly usable as initialization values for the radiotherapy treatment plan optimization algorithm;

automatically initializing, using the generated initial machine parameter settings, a radiotherapy treatment plan optimization algorithm that simulates radiation beam paths using the initialization values and adjusts machine parameters to satisfy patient-specific dosimetric objectives and constraints; and outputting the optimized radiotherapy treatment plan, including the adjusted machine parameter settings, in a format executable by a radiotherapy apparatus to deliver the prescribed dose distribution to the patient.

2. A machine learning system which has been trained according to claim 1, the machine learning system being arranged to take input data in the form of one or more desired reference dose distributions and output a set of machine parameter settings including at least one machine parameter setting that is suitable for producing the one or more desired reference dose distribution by the radiotherapy delivery apparatus.

3. A computer-based method for determining machine parameter settings for a radiotherapy delivery apparatus, using a machine learning system according to claim 2, the method comprising:

inputting one or more reference dose distributions into the machine learning system;

initializing parameters, by the machine learning system; and outputting, from the machine learning system, a set of machine parameter settings for the radiotherapy delivery apparatus.

4. The method of claim 3, wherein the set of machine parameter settings includes Multi Leaf Collimator leaf settings.

5. The method of claim 3, wherein the set of machine parameter settings includes Monitor Unit settings.

6. The method of claim 3, wherein the set of machine parameter settings includes one or more of spot placement, spot weights and beam energy.

7. A method for computer-based radiotherapy treatment plan optimization method including, before performing the plan optimization, performing the method of determining machine parameter settings according to claim 3 and using the resulting at least one machine parameter setting as an initial setting for that machine parameter in the radiotherapy treatment plan optimization.

8. The method of claim 7, wherein the plan optimization is performed by optimizing an optimization problem.

9. The method of claim 8, wherein the plan optimization is performed by dose mimicking.

10. A computer program product comprising computer-readable code means which, when run in a computer will cause the computer to perform the method of claim 1.

11. A computer program product comprising non-transitory storage means having stored thereon computer-readable code means which, when run in a computer will cause the computer to perform the method of claim 1.

12. A computer system comprising a processor and a program memory, the program memory having stored thereon a computer program product according to claim 10.

* * * * *